United States Patent [19]

Iverson et al.

[11] Patent Number: 5,236,825

[45] Date of Patent: Aug. 17, 1993

[54] POLYVALENT METAL ION-CONTAINING ANTIBODY COMBINING SITE CATALYSTS

[75] Inventors: Brent L. Iverson, San Diego; Richard A. Lerner, La Jolla, both of Calif.

[73] Assignee: Scripps Clinic and Research Foundation, La Jolla, Calif.

[21] Appl. No.: 298,082

[22] Filed: Jan. 17, 1989

[51] Int. Cl.$^5$ .................... C12P 21/06; C12N 9/05; C07K 15/28
[52] U.S. Cl. .................. 435/68.1; 435/188.5; 435/219; 435/240.27; 530/388.1
[58] Field of Search ................ 435/219, 212, 68.1, 435/188.5, 240.27; 530/387, 388, 389, 388.1

[56] References Cited
U.S. PATENT DOCUMENTS
5,030,717  7/1991  Tramontano et al. ............. 530/387

OTHER PUBLICATIONS

Schepartz; A. et al. (1987) J. Am. Chem. Soc. 109, 1814–1826.
Iverson, B. L., et al. (1989) Science 243, 1184–1188.
Anon., Science, 243:1119 (1989).

Primary Examiner—Charles L. Patterson, Jr.
Attorney, Agent, or Firm—Dressler, Goldsmith, Shore, Sutker & Milnamow, Ltd.

[57] ABSTRACT

A catalytic molecule comprising a receptor molecule containing an antibody combining site that immunologically binds to a plurality of polyvalent metal ion-containing coordination complexes is disclosed. The coordination complex of a first immunoligand is kinetically inert, whereas the coordination complex of a second immunoligand is kinetically labile. The receptor molecule catalyzes a reaction of the second immunoligand. Immunogens, antigens, and methods of making and using the catalytic receptors are disclosed, as are receptor molecules that catalyze the hydrolysis of a predetermined peptide bond.

4 Claims, 5 Drawing Sheets

POLYVALENT METAL ION-CONTAINING ANTIBODY COMBINING SITE CATALYSTS

DESCRIPTION

1. Technical Field

The present application relates to immunogens, antibodies and antigens, and more specifically to antibody combining site-containing receptor molecules that bind to and catalyse a chemical reaction in an antigenic immunoligand that includes a polyvalent metal ion.

2. Background of the Invention

Binding phenomena between ligands and receptors play many crucial roles in biological systems. Exemplary of such phenomena are the binding of oxygen molecules to deoxyhemoglobin to form oxyhemoglobin, and the binding of a substrate to an enzyme that acts upon it such as between a protein and a protease like trypsin. Still further examples of biological binding phenomena include the binding of an antigen to an antibody, and the binding of complement component C3 to the so-called CR1 receptor.

Many drugs and other therapeutic agents are also believed to be dependent upon binding phenomena. For example, opiates such a morphine are reported to bind to specific receptors in the brain. Opiate agonists and antagonists are reported to compete with drugs like morphine for those combining sites.

Ligands such as man-made drugs, like morphine and its derivatives, and these that are naturally present in biological systems such as endorphins and hormones bind to receptors that are naturally present in biological systems, and will be treated together herein. Such binding may lead to a number of the phenomena of biology, including particularly the hydrolysis of amide and ester bonds as where proteins are hydrolyzed into constituent polypeptides by an enzyme such as trypsin or papain, or where a fat is cleaved into glycerine and three carboxylic acids, respectively, or the synthesis of a non-proteinaceous compound such as cholesterol.

Slobin, *Biochemistry*, 5:2836-2844 (1966) reported preparing antibodies to a p-nitrocarbobenzoxy conjugate of bovine serum albumin. Those antibodies were thereafter used to hydrolyze p-nitrophenyl acetate and epsilon-aminocaproate esters. The reaction of the acetate ester was described by a second-order rate constant and was said to appear to be nonspecific. The second-order rate constant obtained using normal gamma globulin was said to be about equal to that of the specially prepared antibodies. The presence of the specially prepared antibodies was said to inhibit the hydrolysis of the aminocaproate ester.

Kohnen and co-workers also reported attempts using antibodies to catalyze esterolysis. The antibodies utilized by this group were, in each instance, raised to a portion of the ultimately utilized substrate molecule that did not contain the bond to be hydrolyzed.

In their initial work [*FEBS Letters*, 100:137-140 (1979) and *Biochim. Biophys. Acta*, 30 629:328-337 (1980)]anti-steroid antibodies were used to hydrolyze 7-umbelliferone (7-hydroxycoumerin) esters of a carboxyethyl thioether of a steroid. In each instance, an increase in hydrolytic rate was observed as compared to background or to a rate obtained with normal IgG. In both instances, turn over numbers were low (about one mole of substrates per mole of antibody per minute, or less), and the reaction rates declined with time, reaching a plateau with saturation of the antibody. That slow down in rate was attributed to an irreversible binding of the steroidal acid product to the antibody.

Kohen et al. also reported hydrolyses of 7-[-N-(2,4-dinitrophenyl)-6-aminohexanoyl]-coumerin using monoclonal antibodies raised to the dinitrophenyl portions of that substrate molecule [*FEBS Letters*, 111:427-431 (1980)]. Here, a rate increase over background was also reported, but the reaction was said to be stoichiometric rather than catalytic. A decrease in rate that approached zero was reported as saturation of the antibody was reached. Again, the decrease was attributed to product inhibition caused by binding of the product acid to the antibody since some of the initial hydrolysis activity could be regenerated by chromatography of an antibody-substrate-product mixture.

When strong antibody binding is directed to stable states of substrate molecules, the slow rate of dissociation of the complex will impede catalysis. Such is thought to be the situation for the results reported by Kohnen and co-workers.

The above constructs, though interesting, are severely limited by the failure to address the mechanism of binding energy utilization which is essential to enzymes [W. P. Jencks, *Adv. Enzymol.*, 43, 219 (1975)].

Those deficiencies can be redressed by using a transition state analog as the hapten to elicit the desired antibodies. This hapten can assume the role of an inhibitor in the catalytic system.

Thus, immunological binding can be used to experimentally divert binding interactions to catalytic processes. For example, it was suggested that use of an antibody to a haptenic group that resembles the transition state of a given reaction should cause an acceleration in substrate reaction by forcing substrates to resemble the transition state. Jencks, W. P., *Catalysis in Chemistry and Enzymology*, page 288 (McGraw-Hill, New York 1969). Notwithstanding that broad suggestion, specific transition state haptens were not suggested, nor were specific reactions suggested in which the concept might be tested.

Hydrolysis of amide and ester bonds is thought by presently accepted chemical theory to proceed in aqueous media by a reaction at the carbonyl carbon atom to form a transition state that contains a tetrahedral carbon atom bonded to (a) a carbon atom of the acid portion of the amide or ester, (b) two oxygen atoms, one being from the carbonyl group and the other from a hydroxyl ion or water molecule of the medium, and (c) the oxygen atom of the alcohol portion of an ester or the nitrogen atom of the amine portion of an amide. Transition states of such reactions are useful mental constructs that by definition, cannot be isolated, as compared to intermediates, which are isolatable.

Although the above hydrolytic transition states can not be isolated, a large amount of scientific literature has been devoted to the subject. Some of that literature is discussed hereinafter.

Whereas the before-described transition state for amide and ester hydrolyses is believed to be well understood, the parameters of the topology, e.g., size, shape and charge, of receptor combining sites in which particular amides, such as proteins, or esters, such as fats, react through those transition states is not as well understood. It would therefore be beneficial if the topology of a plurality of combining sites were known so that the interactions of the ligands that bind in those sites could be studied. Unfortunately, the topology of receptor combining sites in biological hydrolyses is generally unknown, except for a relatively small number of enzymes whose X-ray crystal structures have been determined.

This lack of knowledge of combining site topology stems in part from a lack of knowledge of even the location in cells of many combining sites of receptors. In addition, for those receptor combining sites whose location is known, the chemical identity; i.e., protein and carbohydrate composition, of the combining site is generally unknown. Thus, the investigator is generally stymied in seeking to understand the topological requirements of receptor combining sites and therefore in seeking to construct therapeutic agents that can fulfill those requirements.

Investigators must therefore screen potential therapeutic agents in animal or cell culture studies to ascertain whether a potential therapeutic agent may be useful. Such systems, while useful, are expensive and time-consuming to use.

Even where the topology and chemical reactivity of a hydrolytic receptor such as an enzyme are known, enzymes such as hydrolytic proteases typically cleave their substrates, polypeptide chains, adjacent to a particular amino acid residue that may occur several times in the polypeptide chain of the protein. While such relatively random cleavage can be useful in obtaining a polypeptide map of the protein, that relatively random cleavage is not as useful where particular amino acid residue sequences are desired to be produced.

For example, modern genetic engineering techniques have been useful in preparing fusion proteins that contain a desired protein or polypeptide fused to the transcription product of a vector gene such as the lac z gene. The use of such fusion proteins is, however, hindered by the presence of fragments of the vector gene product. It would also therefore be beneficial if proteolytic enzyme-like molecules could be developed that would cleave such fusion products between the wanted and unwanted fusion polypeptide or protein portions.

Recently, Lerner, Tramontano and Janda [Tramontano et al., *Science*, 234, 1566 (1986)] reported monoclonal antibodies that catalytically hydrolyzed an ester. Tramontano and Lerner, also describe using monoclonal antibodies to hydrolyze esters in U.S. Pat. No. 4,656,567. Pollack, Jacobs and Schultz [*Science*, 234, 1570 (1986)] reported a myeloma protein denominated MOPC167 [Leon et al., *Biochem.*, 10, 1424 (1971)]that catalyzes the hydrolysis of a carbonate.

In the two Lerner and Tramontano disclosures, the antibodies were raised to a phosphonate that was synthesized to represent a stable analog of the tetrahedral hydrolytic transition state of the carboxylic acid ester or carbonate ester. The Pollack et al. antibody principally discussed was a myeloma protein that happened to bind to a phosphonate that was structurally analogous to the carbonate analog hydrolyzed. Thus, in the Lerner and Tramontano et al. work, the substrate to be hydrolyzed was preselected, with the immunizing analog and hydrolytic antibodies being synthesized in accordance with the desired product. Pollack et al. designed the substrate to be hydrolyzed once they knew the specificity of the myeloma protein. Pollack et al. also reported (above) the existence of a catalytic antibody, substrated and analog substrate system for carbonate hydrolysis similar in concept to that of Lerner et al. Work relating to that system is reported in Jacobs et al., *J. Am. Chem Soc.*, 109, 2174 (1987).

Published patent application WO 85/02414 discusses the possible use of antibodies as catalysts, and presents data relating to the use of polyclonal serum in hydrolyzing o-nitrophenyl-beta-D-galactoside. The antibodies useful in that application are said to be inducible by a reactant, a reaction intermediate or to an analog of the reactant, product or reaction intermediate. The term "analog" is there defined to encompass isomers, homologs or other compounds sufficiently resembling the reactant in terms of chemical structure that an antibody raised to an analog can participate in an immunological reaction with the reactant but will not necessarily catalyze a reaction of the analog.

The data provided in that specification only indicate that some cleavage of the substrate (reactant) galactoside occurred over an eighteen hour time period using a relatively concentrated antibody preparation (1:10 and 1:20 dilutions). Although catalysis was alleged, catalytic activity was not shown since no turn over of the allegedly catalytic antibody was shown, nor was there an indication of the percentage of substrate galactoside cleaved. That application did indicate that beta-D-galactosidase cleaved about ten times as much substrate as did the polyclonal antibodies, presuming linearity of absorbance at the unnamed concentration of substrate studied.

From the data presented in that application, it is possible that a nucleophilic replacement of the o-nitrophenyl group occurred by a terminal amino group of a lysine residue of the antibody preparation used. Thus, the observed absorbance could have been due to formation of epsilon-amino lysinyl o-nitrophenyl aniline or to the formation of an epsilon-amino-lysinyl galactoside and o-nitrophenol, either of which occurrences would not be catalytic since the antibody was consumed, rather than turning over.

In more recent work, bimolecular amide formation catalyzed by antibody molecules has been disclosed [Benkovic et al., *Proc. Natl. Acad. Sci.* USA, 85:5355 (1988)], as has an antibody-catalyzed Claisen rearrangement [Jackson et al., *J. Am. Chem. Soc.*, 110:4841 (1988)]. Stereospecificity was shown in an antibody-catalyzed lactone-forming reaction [Napper et al., *Science*, 237:1041 (1987)]and in an antibody-catalyzed Claisen reaction [Hilvert et al., *Proc. Natl. Acad. Sci. USA*, 85:4953 (1988)].

Rearden et al., Nature, 318:266–268 (1985) and Meares et al. U.S. Pat. No. 4,722,892 describe antibodies that bind to chelated metal ions. Ethylenediaminetetraacetic acid (EDTA) and its derivatives were specifically illustrated bidentate chelating agents.

The specificities of the antibodies described in both the Reardon et al. paper and Meares et al. patent were reportedly particular for a metal ion chelated with EDTA identical to the immunizing EDTA-chelated metal ion except for the absence of linking group used to bind the EDTA-chelated metal ion to keyhole limpet hemocyanin (KLH) to form an immunizing conjugate. Changing the metal ion in the chelate resulted in differences of association constant ($K_a$) between the antibody and chelated metal ion of as much as $10^3$. The Meares et al. patent teaches that its antibodies have a $K_a$ for the complex which is at least about ten times greater than the $K_a$ for the chelating agent alone or its complex with another metal.

Neither of the Rearden et al. or Meares et al. teachings includes the concept of using their antibodies as catalysts as is hereinafter disclosed. Those teachings also therefore could not contemplate the use of kinetically inert coordination complex as an immunogen and a kinetically labile coordination complex as a reactive antigen as is also disclosed hereinafter. Still further differences between those disclosures and the present invention will be apparent from the description that follows.

The before-noted paper by Tramontano et al., *Science,* 25 234:1566–1570 (1986) also teaches hydrolytic reactions catalyzed by antibodies raised to a phosphonate-containing transition state analog of the proposed hydrolytic substrate. One of the analogs contained a dipicolinic acid derivative covalently bonded near the phosphonate group that mimicked the scissile tetrahedral carbonyl carbon atom. The dipicolinic acid group was said to be designed to include a polyvalent metal ion coordination site by analogy with a metalloenzyme model for hydrolysis reactions. Although antibodies induced by that transition state analog were capable of catalyzing hydrolysis of antigenic esters, that catalytic hydrolysis was carried out in the absence of a polyvalent metal ion, and no further report was made in that paper as to the use of a polyvalent metal ion-dipicolinic acid chelate to assist in catalyzing the hydrolytic reactions studied.

BRIEF SUMMARY OF THE INVENTION

The present invention contemplates antibody molecules referred to herein as receptor molecules, immunogens referred to herein as first or immunizing immunoligands, and antigens referred to herein as second or antigenic immunoligands. A receptor molecule catalyzes a reaction of a second immunoligand molecule. Also contemplated are methods of making and using the above.

More particularly, a catalytic molecule comprising a receptor molecule containing an antibody combining site is contemplated. That receptor immunologically binds to a plurality of immunoligands that each contains a polyvalent metal ion coordination complex. The coordination complex of a first immunoligand is kinetically inert and the coordination complex of a second immunoligand is kinetically labile. The receptor molecule catalyzes a chemical reaction of the second immunoligand, and catalyzes no chemical reaction in the first immunoligand. Preferably, the receptors are monoclonal receptor molecules present in a composition.

A preferred catalytic monoclonal receptor molecule forms an immunocomplex with the first immunoligand having a dissociation constant of about $10^{-8}$ or less. The first immunoligand comprises a kinetically inert metal ion coordination complex that contains a first polyvalent metal ion coordinated to two or more individual metal ion coordination ligands. The first of the individual coordination ligands is uni- or multidentate, and the second of the individual ligands is uni- or bidentate. The second individual coordination ligand further includes a first, unreactive organic structure that contains a chain, ring or chain-substituted ring of at least 10 atoms.

The second immunoligand comprises a kinetically labile metal ion coordination complex that contains a second polyvalent metal ion different from the metal ion of the first coordination complex or of a lower oxidation state of the same metal as the first coordination complex. That metal ion is coordinated to two or more individual metal ion coordination ligands. The first of the individual coordination ligands is uni- or multidentate and has a substantially similar size, ligand coordinating functionality and substantially similar structure to the first coordination ligand of the kinetically inert coordination complex. The second of the individual ligands is uni- or bidentate, and further includes a reactive organic structure that contains a chain, ring or chain-substituted ring of at least 10 atoms in sufficient atomic configurational similarity to the first, unreactive organic structure that the dissociation constant for an immunocomplex formed between the catalytic molecule and the second coordination ligand is at most $10^{-2}$.

Preferably, the coordination number of the metal ion of the second immunoligand is equal to or not less than one less than the coordination number of the metal ion of the first immunoligand. It is also preferred that each of the kinetically inert and kinetically labile metal ion coordination complexes has two or more faces that are relatively hydrophobic and one or two faces that are relatively hydrophilic, and that the relatively hydrophobic faces are provided at least in part by the first coordination ligands.

In particularly preferred practice, the receptor molecule is an absin that catalyzes the scission of a preselected peptide bond of a peptide containing at least 3 amino acid residues. Here, the reactive organic structure of the kinetically labile coordination complex contains a peptide of at least 3 amino acid residues including the residue whose peptide bond is cleaved. The unreactive organic structure of the kinetically inert coordination complex contains a peptide having 3 to about 10 amino acid residues having an amido carbonyl carbon that is linked by a chain of 2 to about 7 atoms to a coordinating functional group and is in a position analogous to the scissile carbonyl carbon of the hydrolyzed peptide bond.

Where the metal ion of the kinetically inert, first immunoligand is Co(III), the metal ion of the kinetically labile, second immunoligand is preferably a member of the group consisting of Zn(II), Fe(III), Co(II), Cu(II), Ga(III), Lu(III), In(III), Ni(II), Mn(II), Al(III), and Mg(II).

In accordance with a method aspect of this invention, a catalytic amount of a before-described receptor molecule is admixed in an aqueous medium with the second immunoligand, and the admixture so formed is maintained for a period of time sufficient for the reaction desired to proceed.

It is convenient to discuss the catalyzed reaction in terms usually used for describing enzyme reactions. Using that terminology, the receptor molecule is analogous to the enzyme, and the second immunoligand is constituted by a cofactor comprising the polyvalent metal ion and first individual coordination ligand and a substrate that is constituted by the second individual coordination ligand. In a typical reaction, the receptor molecule is present in a catalytic amount and the concentration of cofactor is about 0.1 to about 10 times that of the substrate.

Useful receptor molecules are prepared by immunizing a suitable animal, such as a mouse or other laboratory animal with an inoculum containing a previously described first immunoligand. Typically, the first immunoligand is linked to an antigenic carrier molecule such as KLH for the immunization.

The immunized animals are thereafter screened for the secretion of antibody molecules that bind to (immunoreact with) the first immunoligand alone, or linked to another carrier molecule such as BSA different from the first carrier molecule. Where polyclonal receptor molecues are desired, the antibodies that immunoreact with the first immunoligand are collected. Those collected antibodies are thereafter screened using a before-described second immunoligand, and those that catalyze a desired, predetermined reaction of the second immunoligand are collected for use.

Where the preferred monoclonal receptors are desired, antibody secreting cells such as spleen cells from an animal that secretes antibodies to the first immunoligand are fused with suitable myeloma cells to form hybridomas. The produced hybridomas are typically screened for production of monoclonal antibodies that immunoreact with the first immunoligand. Hybridomas are more importantly screened for their ability to secrete monoclonal antibodies that bind and catalyze the desired, predetermined reaction of the second immunoligand. Those latter hybridomas are then grown and their monoclonal antibodies collected.

The present invention has several benefits and advantages.

Salient of the benefits is that it has for the first time permitted the preparation and use of a non-enzymic catalyst that is capable of catalyzing the hydrolysis of a peptide bond.

Among the advantages of the invention is the fact that its use permits the preparation of catalysts that can be used to catalyze substantially any reaction capable of catalysis by a Lewis acid in an aqueous medium.

Still further benefits and advantages of the invention will be apparent to the skiled worker from the discussion that follows.

BRIEF DESCRIPTION OF THE DRAWINGS

In the drawings forming a portion of this disclosure.

In step a, a standard solid phase protocol using a SASRIN resin (Bachem Biosciences Inc.) and N-fluoren-9-ylmethoxycarbonyl (FMOC) amino acids was used as described in Stewart, J. M. and Young, J. D., in *Solid Phase Peptide Synthesis*, Pierce Chemical Company, Illinois, (1984) page 82, whose disclosures are incorporated by reference.

In step b, 2 equivalents of 3-phenylpyruvate were reductively alkylated onto the deblocked amino-terminal amine of the resin-linked peptide (1 equivalent) using 2.5 equivalents of sodium borohydride in 4:1 THF:$H_2O$ (v:v) as solvent at pH 7.5 to form the secondary amino acid that is racemic as indicated by the wavy line. The reaction was carried out in a shaker apparatus, and after 12 hours was judged to be complete by ninhydrin analysis.

The product of the reductive alkylation was cleaved from the resin in step c using one percent trifluoroacetic acid in dichloromethane (v:v), and the solvent removed in vacuo. The residue was dissolved in water at pH 7.0 and purified using standard techniques by reversed phase FPLC on a PepRPC column eluted with a linear gradient of 0-40 volume percent acetonitrile in water.

The Co(III)(trien)($CO_3$) complex was converted to the diaqua complex cofactor in step d by reaction with 1.2 equivalents of HCl in water.

The diaqua complex of step d (one equivalent) was admixed with the peptide of step c (1.1 equivalents) in water at a pH value of 8.5 for a period of 6 hours in step e. The resulting immunoligand was purified by ion exchange chromotography on CM-50-120 Sephadex eluted with 0.2N KCl. The appropriate fraction was lyophilized to dryness, and the pure product taken up in ethanol.

The N-acyl peptides 2-7 were prepared by acylating similarly prepared peptides. The immunoligands prepared from peptides 2-7 and cofactor were made in situ.

Figure 2:
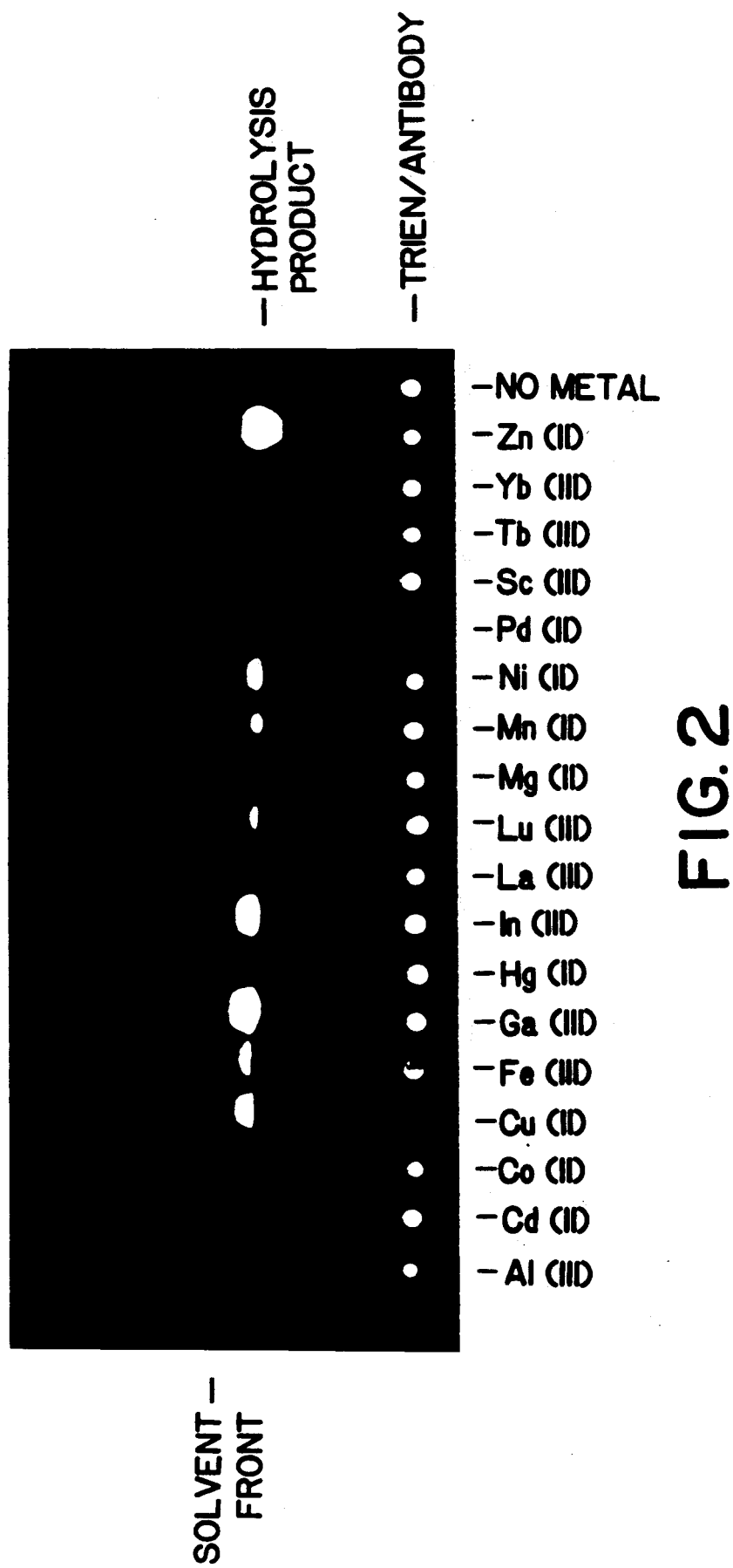
Figure 3A:
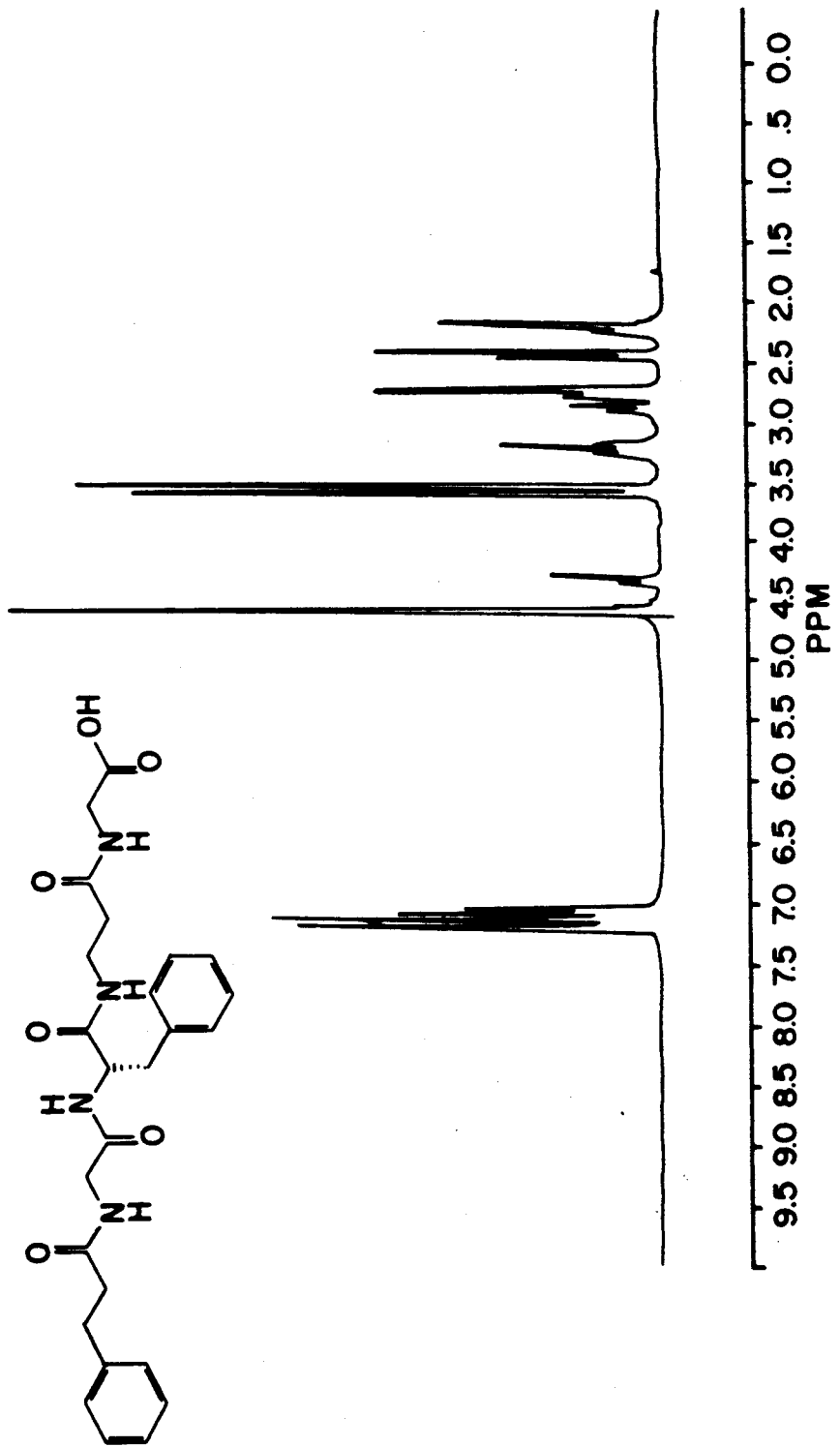
Figure 3B:
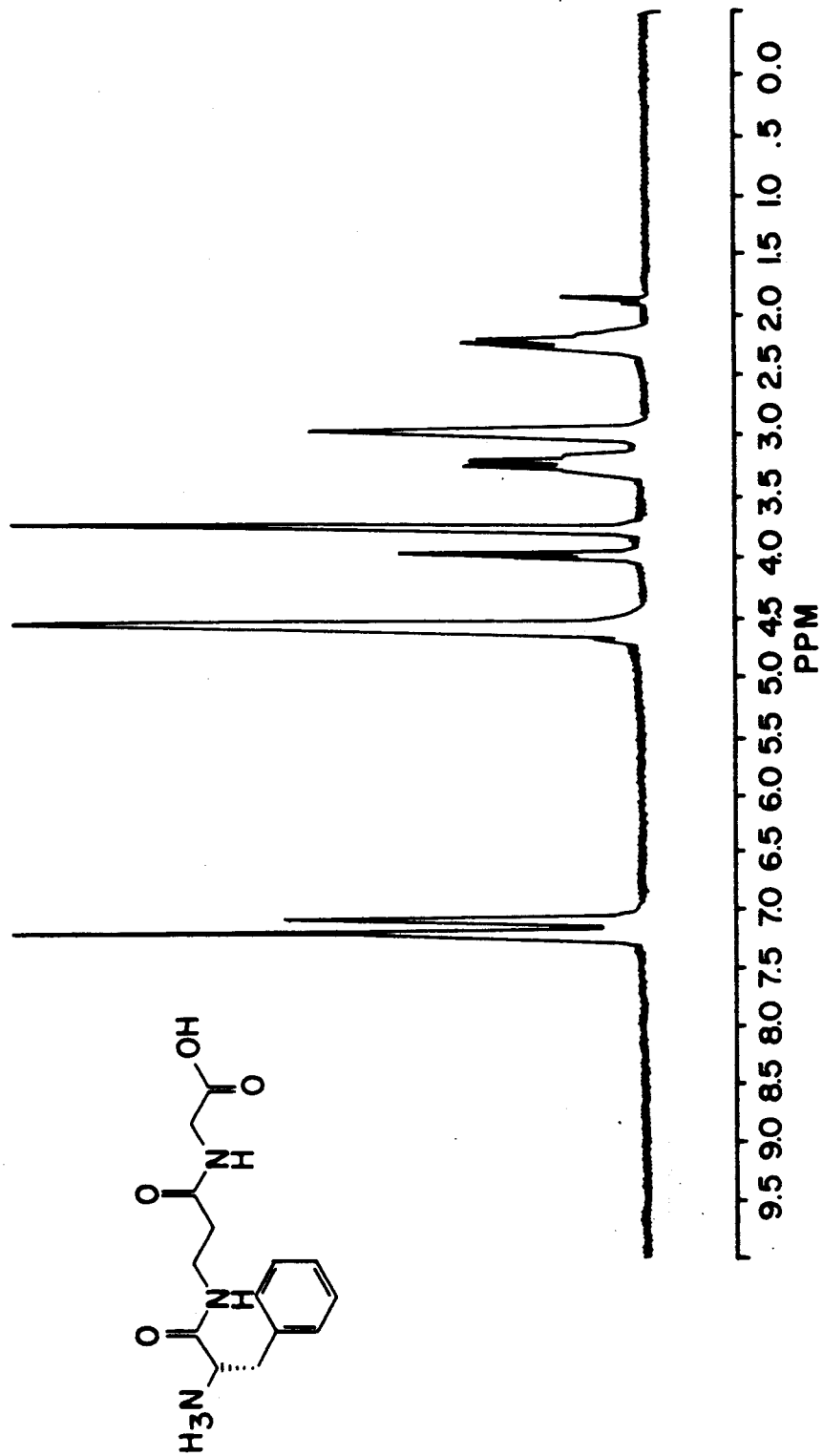
Figure 3C:
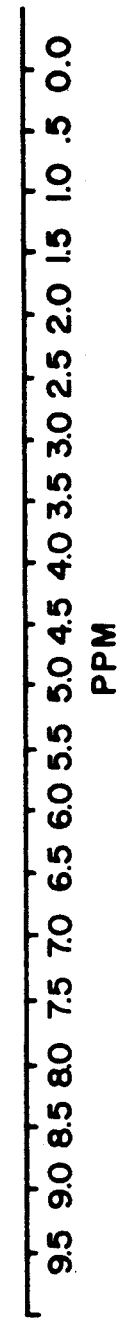
Figure 3C:
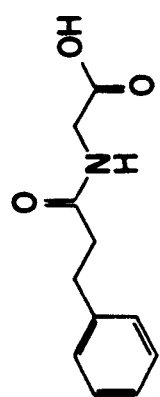

FIG. 2 is a photograph of a thin layer chromatograph that illustrates the receptor 28F11-catalyzed cleavage of an immunoligand comprised of a coordination complex of peptide 2 and a 1:1 polyvalent metal ion-trien.. In each reaction, 10 uM receptor 28F11, 1.2 mM peptide 2 and 3 mM trien-polyvalent metal ion were placed in 50 mM NaCl, 75 mM phospohate buffer at pH 6.5. All reactions were carried out for 5 days at 37° C. An aliquot from each reaction (3.5 microliters; ul) was spotted on a silica thin layer chromatography plate that was eluted with 4:1 methanol:water (v:v). The plate was then sprayed with a 0.2 percent fluorescamine solution in acetone and visualized with long wavelength light. The cleavage product appears as the fluorescamine-reactive material eluting near the solvent front. Receptor and metal-trien remain at the origin. The various metal ions utilized are enumerated along the bottom of the photograph, with the right-hand-most lane illustrating a control reaction that contained the receptor, peptide 2, and trien, but no polyvalent metal ion. The trien reaction with fluorescamine appears attenuated in the reactions containing the colored metal ions Co(II), Cu(II) and Pd(II). Before the reaction, the purified receptor was dialyzed against EDTA to remove metal ions, and all solutions were made with Chelex-treated doubly distilled water. All metal salts used were of the highest purity commercially available.

FIG. 3 contains three panels (3A, 3B and 3C) that are copies of 300 MHz $^1$H NMR spectra in ppm taken in $D_2O$ of peptide 2 (3A) and the two products observed (3B and 3C) in the reaction catalyzed by receptor 28F11 in the presence of Zn(II)(trien). The structures of peptide 2 and the two products are shown in the respective spectra.

DETAILED DESCRIPTION OF THE INVENTION

I. Definitions

The present invention relates to immunogens, antibodies and antigens that involve polyvalent metal ion coordination complexes. Thus, two types of binding phenomena are involved; i.e., (a) between the antibody combining site and its immunogen or antigen, and (b) between the polyvalent metal ion and its coordinated ligand(s). Both types of phenomena are receptor-ligand interactions in a general sense. The discussion that follows immediately below describes the various words and phrases used herein in regard to receptors and ligands The term "receptor" is used herein to mean a biologically active molecule containing an antibody combining site that binds to an immunogen, to an antigen or to a specific inhibitor whose structure resembles the antigen or immunogen. Those receptor molecules are antibodies or paratope-containing antibody portions, and therefore contain an antibody combining site.

Biological activity of a receptor molecule is evidenced by the binding of the receptor to an immunogen, antigen, or inhibitor ligand upon their admixture in an aqueous medium, at least at physiological pH values and ionic strengths. Preferably, the receptors also bind to an immunoligand within a pH value range of about 5 to about 9, and at ionic strengths such as that of distilled water to that of about one molar sodium chloride.

The term "immunoligand" is used herein to mean an immunogen, antigen or inhibitor molecule as noted before that is bound by a receptor molecule.

The above immunoligands each are a polyvalent metal ion coordination complex. Such coordination complexes are generally well known at least in inorganic chemistry, although the complexes contemplated herein are thought to be novel. A polyvalent metal ion coordination complex is sometimes referred to herein as a "coordination complex" or more simply as a "complex".

The polyvalent metal ion of the coordination complexes is coordinately bonded to the functional groups of at least two "coordination ligands", with the maximum number of such coordination ligands being governed by the coordination number of the polyvalent metal ion, as is well known. That coordination number is usually six, although some complexes are known with a coordination number of ten. A coordination ligand will be referred to as such herein, or by a similar phrase, to distinguish such groups from a ligand such as an antigen, immunogen or inhibitor that is bound by an antibody combining site-containing molecule.

Two types of coordination complexes that are referred to as "kinetically inert" and "kinetically labile" are utilized herein. Those terms relate to the kinetic rather than thermodynamic stability of the complexes, and more specifically to relative rates in which coordination ligands can be replaced in each complex. Indeed, some complexes that are thermodynamically unstable in a given medium can persist unchanged for weeks in that medium because they are kinetically inert.

Much of the available evidence pertaining to coordination complexes can be explained on the basis of their electronic configuration as given by the valence bond theory. In general, the labile complexes are either of the outer orbital type or of the inner orbital type with at least one vacant lower d orbital. However, this explanation does not always hold up to experimental results.

Inasmuch as the electronic configuration of a polyvalent metal ion in a coordination complex can be difficult to assess, and is not always predictive, an opertational definition is utilized in the art. A useful operational definition for a kinetically labile complex is that a replacement reaction is complete within the time of mixing; i.e., about one minute, at room temperature using about 0.01 molar solutions. A kinetically inert complex undergoes a replacement reaction at a rate that is either too slow to measure or is slow enough to follow at ordinary conditions by conventional techniques. [Basolo, F. and Pearson, R., *Mechanisms of Inorganic Reactions*, John Wiley & Sons, Inc., New York (1963) page 104, whose disclosures are incorporated by reference.] That operational definition has been refined somewhat in saying that complexes whose reactions may be studied by static methods are inert and faster reactions are labile. [Cotton, F. A., and Wilkinson, G., *Advanced Inorganic Chemistry*, Interscience Publishers, New York (1972) page 653, whose disclosures are incorporated by reference.] The above definition with its refinement is utilized herein.

Additional phrases and terms used herein are defined or explained where they are used.

II. Introduction

A. Overview

The present invention relates to receptor molecules as defined before that immunologically bind to a plurality of immunoligands. The receptor molecules are induced by and therefore bind to an immunogenic, first immunoligand, and also bind to an antigenic, second immunoligand. The receptor molecules catalyze a reaction of the second immunoligand, and thus the receptor molecules share the binding and reaction properties exibited by enzymes.

Each of the immunoligands bound by a receptor molecule contains a polyvalent metal ion coordination complex. The complex of the immunogenic, first immunoligand is kinetically inert, whereas the complex of the antigenic and reactive second immunoligand is kinetically labile.

Antibodies are induced using a first, immunogenic immunoligand that is typically linked to an antigenic (immunogenic) carrier molecule. The antibodies so induced are harvested and assayed for their ability to bind to (immunoreact with) the immunizing, immunoligand linked to a different carrier molecule and/or free in solution as an inhibitor molecule.

Immunoglobulin-producing cells such as those from the spleen of an animal whose antibodies bind to the immunizing immunoligand are collected and are fused with myeloma cells to form hybridoma cells. The hybridoma cells are grown in a culture medium and the supernatant medium from the growing hybridoma cells is assayed again for the presence of antibodies that bind to the immunizing immunoligand.

Hybridoma cells whose supernatant contains such binding antibodies are then screened to determine which of those cells secrete antibodies that also bind to and catalyze a reaction of a second, reactive immunoligand. Hybridoma cells whose secreted antibodies bind to the immunizing, first immunoligand and bind to a reactive, second immunoligand and catalyze a reaction of that second immunoligand are then cloned to provide the desired monoclonal antibodies from culture medium supernatant or from the ascites of a host mammal into which the hybridoma is introduced.

The described monoclonal antibodies can be used as the receptors of this invention. Alternatively, the so-called Fc or Fc' portions of the antibodies can be removed as by enzymic cleavage to provide antibody combining site-containing receptor molecules such as Fab, F(ab')$_2$ or Fab' antibody portions, respectively.

B. Catalytic Antibody/ Enzyme Comparison

Antibodies and enzymes are both proteins whose function depends on their ability to bind specific target molecules. Enzymatic reactions differ from immunological reactions in that in an enzymatic reaction the binding of the enzyme to its substrate typically leads to chemical catalysis, whereas a non-catalytic complex is the usual result of antibody-antigen binding.

Enzymes are believed to catalyze reactions such as the hydrolysis of proteins by combining with the protein to stabilize the transition state of the hydrolysis reaction. It is generally believed that the rate of an enzymatic reaction is increased relative to the rate of a non-enzymatic reaction because of the ability of the enzyme to stabilize the transition state of the reaction; i.e., to reduce the free energy of the transition state, and thus, the free energy of activation, of the reaction [Jencks, W. P., *Adv. Enzymology*, 43, 219 (1975) and Pauling, L., *Amer. Scientist*, 36, 58 (1948)]. Support for this theory comes from the observation that substances that are thought to model the presumed transition states are often strongly bound to the enzymes as competitive inhibitors. Leinhard, G., *Science*, 180, 149 (1973) and Wolfenden, R., *Acc. Chem. Res.*, 5, 10 (1972). It is further thought that the enzyme accomplishes this lowering of the reaction free energy by binding the transition state geometry of the reactant more strongly than it binds to the corresponding substrate(s) or product(s).

This means that the intrinsic binding energy of the enzyme is much greater than can be measured from the binding of substrates or products. Essentially, the binding energy of the enzyme is utilized to perform the chemical reaction [Jencks, W. P., *XVII International Solvay Conference* (November 1983)].

The converse proposition is that an antibody that is prepared to optimally bind a suitable analog of a transition state would function as a catalyst. The demonstration of this result by Lerner and co-workers and Schultz and coworkers in the previously cited papers and those below completes the correlation of enzyme function and antibody structure and provides a useful approach to devising artificial enzymes.

Thus, as noted before, monoclonal antibodies have been elicited capable of catalyzing a number of chemical reactions including ester hydrolysis [Tramontano et al., *Science* 234: 1566 (1986) and Tramontano et al., *J. Am. Chem. Soc.* 110: 2282 (1988)], carbonate hydrolysis [Pollack et al., *Science* 234: 1570 (1986) and Jacobs et al., *J. Am. Chem. Soc.* 109: 2174 (1987)], a stereospecific lactonization reaction [Napper et al., *Science* 237: 1041 (1987)], bimolecular amide formation [Benkovic et al., *Proc. Nat. Acad. Sci. USA*, 85: 5355 (1988) and Janda et al., J. Am. Chem. Soc., 110: 4835 (1988)], a Claisen rearrangement [Jackson et al., *J. Am. Chem. Soc.* 110:4841 (1988) and Hilvert et al., Proc. Nat. Acad. Soc. USA, 85:4953 (1988)], hydrolysis of a p-nitroanilide amide [Janda et al., *Science*, 110:7888 (1988)]and a photochemical cleavage of thymine dimers [Cochran et al., *J. Am. Chem. Soc.*, 110:7888 (1988)]. Recently, a system was also reported in which a cofactor moiety was covalently attached to an antibody binding site [Pollack et al., *Science* 242: 1038 (1988)].

Most of the above catalytic antibodies were produced by immunizing an animal with a "transition state analog" compound that in both shape and charge distribution resembles, a high energy structure thought to occur along the reaction pathway. The resulting antibodies then catalyzed the desired reaction presumably by utilizing binding forces to lower the energy of the high energy structure, thus lowering the overall reaction barrier. In some instances, chemically reactive amino acid residue side chains in the antibody binding sites have been implicated in the catalyzed reaction. [Janda et al., *Science* 241:1188 (1988); Cochran et al., *J. Am. Chem. Soc.* 110:7888 (1988) and Tramontano et al., *Proc. Nat. Acad. Sci. USA*, 83: 6736 (1986).]

The mechanism by which an antibody hydrolyzes an ester or amide bond of a bound substrate ligand described above can be thought of in terms of an "induced fit" model. As the loosely bound substrate distorts or rearranges to conform to the binding geometry of the antibody, stress can be relieved by chemical reorganization of a single, predetermined amide or ester bond such that this reorganization leads to the hydrolysis of the bond.

Metal ion participation in amide bond hydrolysis has been observed in both enzymatic [Lipscomb, *Acc. Chem. Res.*, 15:232 (1982) and Mathews, *Acc. Chem. Res.*, 21:333(1988)] and model systems [Collman et al., *J. Am. Chem. Soc.*, 85:3039 (1963); Buckingham et al., *J. Am. Chem. Soc.*, 92:6151 (1970); Schepartz et al., *J. Am. Chem. Soc.*, 109:1814 (1987) and Groves et al., J. Am. Chem. Soc., 106:630 (1984)]. At least two types of interactions between metal and amide have been identified.

In the first type, the metal atom directly coordinates the amide carbonyl oxygen. The resulting polarization of the carbonyl group facilitates nucleophilic attack of hydroxide or water at the carbonyl carbon atom. Another mode of catalysis consists of the delivery of a metal-bound hydroxide or water nucleophile to the carbonyl carbon atom of the amide.

In the case of the stoichiometric Co(III)-promoted amide hydrolysis in aqueous solution in the pH value range 9-14, both types of interaction were found to significantly increase the rate of nteraction involving the metal-bound hydroxide nucleophile was found to be the more efficient [D. A. Buckingham et al., *J. Am. Chem. Soc.*, 92: 6151 (1970)]. For the Zn(II)-containing protease enzymes thermolysin and carboxypeptidase A, it is possible that both types of interaction are operating to increase the rate of amide hydrolysis [Mathews et al , *Acc. Chem. Res.*, 21:333 (1988) and Christianson et al., *J. Am. Chem. Soc.*, 108:4998 (1988)].

A new approach is disclosed herein whereby an immunoligand comprised of a polyvalent ion metal complex (cofactor) and reactive coordination ligand (substrate) is noncovalently bound by the antibody (receptor) in order to provide chemical reactivity in the antibody combining site. The production and initial characterization of exemplary catalytic monoclonal antibodies (receptor molecules) that can catalyze the site-specific hydrolysis of a glycine-phenylalanine (Gly-Phe) peptide bond at pH 6.5 using various metal ion-containing cofactors is disclosed hereinafter. The term "absin" is used to designate this new class of proteolytic catalytic antibodies.

Using that new approach, it was anticipated and found that a reaction, even one as energetically demanding as peptide hydrolysis, could be mediated by an antibody. Furthermore, the specificity of binding so characteristic of antibody-antigen interactions provided the absins with readily programmable sets of selective profound sequence specificities.

Peptide hydrolysis is but one example of a large number of reactions that could benefit from incorporation of a labile metal ion-containing complex into the antibody combining site of a receptor molecule. The geometric constraints possible with these systems can be exploited to enforce stereoelectronic control on further reactions such as aldol condensations and chiral epoxidations.

III. Receptor Molecules

A receptor molecule of the invention is catalytic and contains an antibody combining site that immunlogically binds; i.e., binds via the paratope in an antibody-antigen relation, to a plurality of immunoligands that each contain a polyvalent metal ion coordination complex. The coordination complex of a first, immunizing immunoligand is kinetically inert, whereas the coordination of a second, antigenic immunoligand is kinetically labile. A receptor molecule of the invention also exhibits immunological binding to portions of the kinetically labile immunoligand such as to a metal ion complex formed from the polyvalent metal ion and a first individual coordination ligand (cofactor), as well as to a second individual coordination ligand in the absence of the polyvalent metal ion (substrate).

Additional polyvalent metal ion-containing coordination complexes (immunoligands) can be bound by a receptor molecule, and can be kinetically inert or labile. That catalyzed reaction is a reaction catalyzed by a Lewis acid, and substantially any reaction catalyzed by a Lewis acid that can be carried out in an aqueous medium can be catalyzed by a receptor molecule as described herein with an appropriate metal ion-containing cofactor. A receptor molecule also catalyzes a chemical reaction of the second imunologiand, but does not catalyze a chemical reaction in the first immunoligand.

The immunizing, first immunoligand itself comprises a kinetically inert metal ion coordination complex that contains a first polyvalent metal ion coordinated to two or more individual metal ion coordination ligands.

A polyvalent metal ion can often exhibit a plurality of three-dimensional shapes of coordination complexes. The shape of the complex depends, inter alia, upon the element, its oxidation state, its coordination number and the ligands that are coordinated to the metal ion. Exemplary useful kinetically inert coordination complexes are formed from Co(III) and Pt(II) that usually form octahedral and square planar complexes, respectively, with saturated amine-containing ligands.

The first of these two or more individual metal ion coordinations can be unidentate or multidentate and can therefore form one or a plurality of coordinate bonds to the metal ion.

Exemplary unidentate ligands include water, ammonia, hydroxide ion, halide ion such as fluoride, chloride, bromide or iodide ions, monocarboxylate ions containing 1 to about 8 carbon atoms, cyanide ion and the like. Those ligands are usually referred to as aqua, ammine, hydroxido, fluoro, chloro, bromo, iodo, monocarboxylato and cyanato, respectively.

Exemplary multidentate ligands include bi-, tri-, tetradentate ligands, and are exemplified by carbonate ion, oxalate ion, 2,2′-bipyridine, ethylenediamine, acetylacetonate ion, 1,10-phenanthroline, 2,2′,2″-triaminotriethylamine, triethylenetetramine and ethylenediaminetetracetate ion. Those ligands are usually referred to as carbonato, oxalate (ox), 2,2′-bispyridine (bipy), ethylenediamine (en), acetylacetonate (acac) 1,10-phenanthroline (phen), 2,2′,2″-triaminotriethylamine (tren), triethylenetetramine (trien), and ethylenediaminetetraacetato (EDTA), respectively, with their usually used abbreviations in parentheses. Quinquidentate and hexadentate ligands are also known.

It is preferred that the first individual coordination ligand be multidentate and capable of forming coordinate bonds with at least half of the available coordination sites. Thus, it is preferred that the first individual coordination ligand of the first, immunizing immunoligand be at least tridentate where the polyvalent metal ion has a coordination number of six as is the case for Co(III) complexes with saturated amines. The trien ligand that is tetradentate is particularly preferred for use with Co(III). A bidentate ligand such as en is preferably used for a metal ion such as Pt(II) that forms square planar complexes with saturated amine ligands.

The second individual coordination ligand of the first complex can be unidentate or bidentate, and further includes a first unreactive organic structure that contains a chain, ring or chain-substituted ring of at least 10 atoms. The liganding functionality of this coordination ligand preferably contains a functional group that is anionic at the pH value at which the ligand is to be used such as a carboxylate group, which is preferred. Other functional groups that can provide the anionic liganding function include phosphonate and hydroximate ions.

The second coordination ligand is largely responsible for providing the specificity of binding and reaction to the catalyst so the coordination ligand selected contains a portion that bears a substantial atomic configurational similarity to the coordination ligand or substrate in which the reaction is catalyzed (discussed hereinafter). Thus, this second, unreactive coordination ligand of the first immunoligand contains a chain, ring or chain-substituted ring that contains at least 10 atoms in addition to the liganding functionality so that this coordination ligand can induce and be bound by the antibody combining site.

An antibody combining site is generally considered to be able to accomodate about five to about seven amino acid residues Since each residue contributes a chain of three atoms, this coordination ligand is minimally about three amino acid residues long, when measured in terms of peptides. The remainder of the combining site is occupied by the polyvalent metal ion and its first, and possibly other, individual coordination ligand.

This unreactive, second individual coordination ligand can be larger than a chain, ring or chain-substituted ring of about 10 atoms, and can be as large as solubility of the immunizing immunoligand in an immunized animal's blood permits. However, when more than about 30 atoms in a chain, ring or chain-substituted ring are used in this ligand, those atoms can be "wasted" in that they either induce antibody molecules that are not useful or do not induce antibodies.

This second coordination ligand is unreactive, as already noted, in that it does not undergo a chemical reaction when in the presence of an antibody induced by its antibodies, except perhaps for the ionziation of one or more protons. However, inasmuch as this coordination ligand is largely responsible for the binding and reaction specificity of the catalyst, this coordination ligand not only structurally resembles the reactive coordination ligand, but includes a bond to the metal liganding functional group about 2 to about 7, and more preferably about 2 to about 5, atoms from a site that is structurally analogous to the site in the reactive coordination at which a desired reaction is to be catalyzed.

Thus, for example, if a bond to a particular carbonyl group is to be broken in the reaction to be catalyzed, the scissile carbonyl group is considered the site of reaction, and the second, coordination ligand of the first immunoligand contains a carbonyl group about 2 to about 7 atoms from the metal liganding functional group. That carbonyl group is also in a structural configuration that is substantially similar to that of the carbonyl group at which the reaction takes place This proximity helps to assure that the site of the reaction to be catalyzed is proximal to the polyvalent metal ion.

The remaining structure of this second, unreactive coordination ligand can be a hydrocarbon or substituted hydrocarbon chain as are found in squalene or a peptide, respectively Ring structures such as those of an aromatic compound such as benzene, naphthalene or pyridine can be included as can smaller cyclic and chain-substituted cyclic compounds such as decalin derivatives, and steroidal derivatives such as those of estradiol, testosterone In a preferred embodiment, the unreactive organic structure is a peptide. Such a peptide can be of the naturally occuring L configuration, of the D configuration, can contain residues such as beta-alanine, and can be a mixture of two or more of such amino acid residues.

It is noted that the second, unreactive coordination ligand is not an analog of the transition state of the reaction to be catalyzed, even though that coordination ligand is largely responsible for providing the binding and reactivity specificity of the receptor molecules. Thus, again, the approach taken herein toward inducing an antibody combining site by design is quite different from the approaches taken previously, as are the receptors and results obtained.

Once the first two coordination ligands are determined, the remaining coordinating positions, if any, are typically filled using unidentate or bidentate ligands such as those discussed before. Water, the aqua ligand, is a particularly preferred coordination ligand for use in completing the coordination complex, if the first and second immunoligands do not fill the coordination sphere of the polyvalent metal ion.

A receptor molecule typically exhibits a dissociation constant Kd, for an immunocomplex formed with a first immunoligand of at least $10^{-8}$. More preferably, that dissociation constant is $10^{-12}$ or less.

The antigenic, second immunoligand comprises a kinetically labile metal ion coordination complex that contains a second polyvalent metal ion that is different from the metal ion of the first immunoligand (coordination complex) or that metal ion is of a lower oxidation state of the same metal as that first metal ion. Thus, where the first polyvalent metal ion is Co(III), the second metal ion is Co(II) or can be an ion such as Zn(II), Ga(III), In(III), Fe(III), Cu(II), Ni(II), Lu(II), Mn(II), Al(III), or Mg(II), or the like. Zinc(II) is particularly preferred where Co(III) is used as the metal ion of the kinetically inert complex. Where the kinetically inert complex contains a metal ion such as Pt(II) that forms square planar complexes Cu(II) is a preferred metal ion of the kinetically labile coordination complex of the second immunoligand.

Although an immunocomplex formed between a receptor molecule and a first immunoligand can be viewed a usual antibody-antigen interaction for which a dissociation constant can be properly expressed, the same is not true for the immunocomplex formed between the receptor and the second immunoligand. The reason for this apparent anomoly stems from the facts that the second immunoligand contains a kinetically labile coordination complex and the second, reactive individual coordination ligand may not have usual coordination ligand functional groups, and may coordinate with the metal ion and first coordination ligand substantially only in the presence of the receptor molecule.

Thus, the second immunoligand tends to behave in a manner similar to an enzyme, substrate, cofactor system in which the receptor is analogous to the enzyme, the second, reactive coordination ligand is analogous to the substrate, and the metal ion and its first coordination ligand (and possible other coordination ligands) are together analogous to a cofactor such as NAD or FAD. The discussion hereinafter will nevertheless usually consider the second immunoligand as a single entity except where clarity of description or explanation is better served by referring to it or its parts as a receptor, substrate and cofactor.

All of the criteria for selecting the polyvalent metal ion of the second immunoligand in addition to the ion forming a kinetically labile coordination complex are not completely understood. However, enough is known so that a useful catalyst can be prepared relatively easily.

First, the metal ion of the kinetically labile complex should be capable of forming a coordination complex of the same shape (geometry) as does the metal ion of the kinetically inert complex. Thus, where Co(III) that forms octahedral complexes with saturated amines is used in the kinetically inert complex, a metal ion that forms octahedral planar complexes with such amines can be used as the metal ion of the kinetically labile complex.

When discussing the shape or geometry of a coordination complex, it is not necessary that the complex be isolatable and its structure determined by X-ray or similar techniques. Rather, the inferential techniques usually used for such structure determinations are adequate.

The coordination numbers exhibited by the second metal ion is equal to that of the first polyvalent metal ion, or not less than one less than the first polyvalent metal ion. Thus, where the first polyvalent metal ion is Co(III) with a coordination number of six, the second polyvalent metal ion exhibits a coordination number that preferably is six, but can be five.

The size of the metal ion also appears to play a role. For example, Co(III) has an ionic radius of 0.63 Angstroms from crystallographic measurements. Four of the metal ions whose coordination complexes did not catalyze the peptide cleavage reaction described hereinafter, Cd(II), Tb(III), Hg(II) and La(III) have similarly measured ionic radii of 0.97, 0.923, 1.10 and 1.02 Angstroms, respectively. On the other hand, each of the useful second polyvalent metal ions noted before has an ionic radius of between 0.51 Angstroms [Al(III)] and 0.85 Angstroms [Lu(III)]. Thus, the ionic radius of a useful second metal ion is ± about one-third that of the metal ion of the kinetically inert complex, whereas the ionic radii of metal ions that were not useful were about one-half again or more larger than that of the polyvalent metal ion kinetically inert complex. [Crystal ionic radii from *Handbook of Chemistry and Physics*, Weast, ed., 54th ed., CRC press, Cleveland (1973) pp F-194-195.]

The above four criteria; i.e., (1) size (ionic radius) about ± one-third that of the metal ion of the immunizing immunoligand, (2) formation of a kinetically labile complex that (3) has the same geometry and (4) same coordination number as the kinetically inert complex when the same first, individual coordination ligand is used, appear to be useful for selecting an operable metal ion. Thus, a useful metal ion typically fulfills those criteria, although some useful metal ions may not.

Those criteria are therefore sufficient to define most, but not every metal ion that is useful. For example, the Yb(III) ion has an ionic radius of 0.86 Angstroms and can meet the other three criteria, but failed to provide catalysis. Nevertheless, the skilled worker using the above criteria can readily obtain catalytic results.

The first individual coordination ligand of the kinetically labile metal ion complex is unidentate or multidentate, preferably is multidentate, and more preferably has the same number of coordination liganding functional groups as does the first individual coordination ligand of the kinetically inert metal ion complex. In addition, this first coordination ligand also has a substantially similar size and structure, and same type of ligand coordinating functionality as the first individual coordination ligand of the kinetically inert metal ion complex.

It is thus more preferred that where the first coordination ligand of the kinetically inert complex is uni-, bi-, tri- or tetradentate, the corresponding first coordination ligand of the kinetically labile complex be uni-, bi- ,tri- or tetradentate, respectively. Similarly, the coordination bond-forming functional groups, e.g., saturated amine, unsaturated amine, carboxylate, enolate, phosphine or the like, of that first coordination ligand of the immunizing, kinetically inert complex are also present in the first coordination ligand of the second, antigenic, kinetically labile complex.

The substantial similarity in size and structure of the two first coordination ligands, as well as the sameness of dentation and liganding functionality, relate to a relative immunological sameness between the two (kinetically inert and labile) complexes. Thus, if these ligands are substantially different in size and of substantially different structure and bonding type, the second immunoligand may not be bound by an antibody induced by the first.

It is well known that the change of even a single amino acid residue in a polypeptide sequence can mean the difference between a given antibody binding to one sequence and not to another. It is also well known that antibody binding requirements are normally not that stringent and amino acid side groups that possess similar sizes or functionalities can usually replace each other with minimal effects on antibody binding.

Thus, an aspartic acid or amide can usually replace a glutamic acid or amide, respectively, as can an arginine and lysine, or alanine, leucine and isoleucine replace each other, and the like. Still further, Houghten, *Proc. Natl. Acad. Sci. USA*, 82:5131 (1985) reported that each of twelve of the thirteen residues of a particular polypeptide could be individually exchanged for any of the other nineteen natural amino acids while keeping the other residues constant without substantially impairing the ability of a monoclonal antibody to bind to the thirteen residue peptide of altered structure.

There is consequently some scope for differences in size and shape, as well as in its number and type of liganding functionality between the two first coordination ligands. That difference can be expressed in terms of a dissociation constant of the binding complex of the receptor molecule and the cofactor formed by the polyvalent metal ion and first, individual coordination ligand. Dissociation constants between a useful receptor molecule and cofactor alone have not been measured, but appear to be about one or three orders of magnitude greater than those of the same receptor and an immunizing first immunoligand, depending upon the receptor molecule and polyvalent metal ion selected for study.

The kinetically labile coordination complex formed from the above, second polyvalent metal ion and its first, individual coordination ligand constitutes the cofactor, when using the receptor, cofactor and substrate terminology for the second immunoligand. One or more additional coordination ligands such as aqua coordination ligands can also be present as part of the cofactor.

The second of the individual coordination ligand (the substrate) of the kinetically labile, second immunoligand is unidentate or bidentate and includes a reactive organinc structure containing a site for the reaction catalyzed. However, the liganding functionality need not be the same as that of the second individual coordination ligand of the kinetically inert complex, and preferably is different.

Indeed, the liganding functionality need not be a usual coordination ligand bond-forming functional group. Rather, the coordination ligand bonding that occurs can be forced by the binding (entropic) effect of the receptor molecule combining site and metal ion-containing cofactor. For example, the liganding functional groups of the illustrative bidentate second coordination ligand peptide of the immunizing immunoligand discussed hereinafter are a secondary amine and carboxylate group, whereas the reactive second coordination ligand (substrate) used has neither group but does possess an amido group at the analogous position to the secondary amine.

The second individual coordination ligand (substrate) further includes a reactive organic structure that contains a chain, ring or chain-substituted ring of at least 10 atoms that is of sufficient atomic configurational similarity to the first, unractive organic structure that the dissociation constant for an immunocomplex between the receptor molecule and this second coordination ligand is at least $10^{-2}$ or less, as measured in the absence of the metal ion-containing first coordination complex (cofactor). Preliminary results for one such immunocomplex between a receptor and a substrate have provided a dissociation constant on the order of $5\times10^{-3}$.

There is no presently known upper limit on the size of the second, reactiave coordination ligand (substrate) other than its solubility in the medium in which the reaction is to be carried out, e.g. an aqueous medium. For example, a receptor molecule of this invention can be used as a peptidase to cleave a predetermined peptide bond between the termini of a protein. In that instance, the whole protein or a smaller portion thereof can be used as the second, reactive coordination ligand.

Thus, the second, reactive organic structure that comprises the second individual coordination ligand of the kinetically labile complex (the substrate) is sufficiently similar in structure to the second, unreactive organic structure of the kinetically inert complex to be bound by the catalyst. Most preferably, the two second individual coordination ligands have the same organic structures within a chain of about 10 atoms adjacent to the site at which the catalyzed reaction takes place.

The site at which a catalyzed reaction takes place is typically a carbonyl group as in an amide or ester cleavage reaction or a ketone or aldehyde group as in an aldol condensation. Carbon atoms of ethylenic double bonds can also be the site at which the catalyzed reaction takes place.

The reactions catalyzed by a receptor molecule are carried out in aqueous media in which a water molecule or hydroxide ion takes part in the reaction and serves as an additional coordination ligand for the polyvalent metal ion. Thus, access of water or hydroxide ion to the receptor-second immunoligand immunocomplex can be of some import.

That access, where desired, can be facilitated by providing the immunizing, first immunoligand with relatively hydrophobic and hydrophlic areas. Since metal ion complexes such as octahedral, trigonal bipyramidal and tetrahedral complexes can be viewed as three-dimensional structures or polydrons, it is convenient to describe relatively hyrophobic or hydrophilic areas as the faces of a polydron, with the coordinate ligand-binding functional groups at the apices.

For example, the three ethylene groups of the trien molecule together with the peptide and phenyl ring portions of the immunizing and second immunoligands discussed hereinafter provide relatively hyrophobic faces to those complexes. The primary and secondary amine portions of those ligands provide relatively more hydrophilic apices. However, the anionically charged carboxylate functional group of the second coordination ligand of the first immunoligand is more hydrophilic than those amines, and since it is at a terminus of a ligand provides a relatively hydrophilic apex and adjacent face or faces to the first immunoligand. That relatively hydrophilic face was expected to be oriented toward the outside or water-side of a resulting receptor-containing immunocomplex, with the relatively more hydrophobic portion (faces) directed toward the inside surface of the antibody combining site of that immunocomplex.

Thus, the exemplary receptor molecules used herein were designed to provide relatively easy access of water or a hydroxide ion to the immunocomplex. That relatively easy access was further facilitated by designing the second immunoligand to contain fewer coordination ligand binding functional groups than were present in the immunizing immunoligand. Consequently, with a second metal ion of about the same size and the same coordination number as the first metal ion, and with fewer available coordination ligandable functional groups, a water molecule or hydroxide ion from the aqueous reaction medium could readily provide an aqua or hydroxido ligand to complete the coordination sphere of the kinetically labile metal ion complex.

The above strategy of utilizing metal ion complexes having two or more relatively hydrophobic faces and one or more relatively hydrophilic faces, coupled with utilizing a second immunoligand having at least one fewer ligand bond-forming functional groups is general to providing an aqua or hydroxido ligand to the immunocomplex formed by the receptor and second immunoligand in an aqueous medium.

The use of an anionically charged coordination ligand functional group in the first, immunizing immunoligand that is not present in the reactive, antigenic, second immunoligand can be advantageous. Thus, that use can help to provide a hydrophilic apex and adjacent face to the second immunoligand by inducing a positively charged residue, e.g. argine, lysine or histidine, in the combining site, which in turn induces a charge-balancing hydroxide ion where no anionically charged functional group is present in the coordination ligand.

IV. Methods

A method aspect of the present invention contemplates the catalysis of a predetermined chemical reaction using a receptor molecule as described herein. A reaction catalyzed by such a receptor molecule proceeds in water, at an optimal pH value and one atmosphere of pressure at a rate that is typically at least $10^3$ times faster than that reaction proceeds under the same conditions of temperature, pressure, pH value and substrate concentration in the absence of receptor and cofactor molecules. Preferably, the rates are different by a factor of at least $10^4$.

For example, Kahne, *J. Am. Chem. Soc.*, 110:7529 (1988) reported that the half-time for spontaneous hydrolysis of a peptide bond in neutral water is about $3\times10^{-9}$ $sec^{-1}$, or about 7 years. On the other hand, peptide 2 (discussed hereinafter) as substrate was completely hydrolyzed at pH 6.5 at 37° C. after eight days using a receptor of this invention and a metal ion-containing cofactor.

In accordance with a method of the invention, an effective amount of before-described receptor molecules are admixed with an antigenic, second immunoligand (as before-described) in an aqueous medium to form an admixture. That admixture is maintained for a time period sufficient for the desired, predetermined reaction to proceed. The product(s) of the reaction can thereafter be isolated, if desired, as can be the receptor molecules.

A method of this invention utilizes an aqueous medium as a portion of the reaction admixture. That medium typically contains water and buffer salts. In addition, the medium can contain other salts such as sodium choride, as well as water-soluble calcium and magnesium salts as are frequently found in protein-containing media. Organic solvents such as methanol, ethanol, acetonitrile, dimethyl sulfoxide, dioxane, hexamethylphosphoramide and N,N-dimethylforamide can also be present. Surface active agents that emulsify the reactant ligand and receptor molecule can also be present. The critical feature of ingredients present in the aqueous medium is that those ingredients not substantially interfere with or inhibit the catalytic reaction as by denaturation of the receptor molecule. Additionally, the aqueous medium is substantially free from salt, proteins generally, and enzymes, specifically, that inhibit the reaction catalyzed by the receptor molecule.

The aqueous medium typically has a pH value of about 5 to about 9, and preferably about pH 6.0 to about 8.0. pH Values greater and less than those recited values can also be utilized so long as the catalyzed reaction is again not substantially interfered with or inhibited.

The catalytic reactions are typically carried out at ambient room temperature; i.e., at about 20 to about 25 degrees C., or at 37 degrees, and at an ambient atmospheric pressure; i.e., at about one atmosphere. However, temperatures down to about the freezing point of the aqueous medium and up to about the boiling point of the medium at atmospheric pressure can also be used. As is known, proteins such as the receptor molecule tend to denature at elevated temperatures such as those at which an aqueous medium boils, e.g. at about 100 degrees C., and thus temperatures below about 40 degrees C. are preferred. As is also well known, reactions that follow multimolecular kinetic expressions decrease in rate as the temperature decreases. Thus, a minimal temperature of about 15 degrees is preferred.

The admixture formed from the receptor, cofactor and substrate is maintained as above for a time period sufficient for the desired, predetermined reaction to proceed. That maintenance time can be a matter of seconds to days or weeks, and depends, inter alia, upon the particular receptor molecule, cofactor and substrate molecules, reaction temperature and pH value, as well as whether one is seeking the product or examining reaction kinetics. In the exemplary reactions discussed hereinafter, maintenance times of 5 and 8 days were utilized where products were desired to be shown and isolated, respectively, and times of minutes and hours are used for kinetic determinations.

The substrate (second coordination ligand of the second immunoligand) is present in a reaction mixture in an amount up to its solubility in the aqueous medium. A two phase system that includes insoluble substrate can also be used, but normally is not so used. Normally used concentrations of the substrate are about 0.1 micromolar (uM) to about 10 millimolar (mM). Where the product is desired, per se, relatively higher concentrations are used as compared to lower concentrations where a reaction mechanism or reaction kinetics are to be studied.

An effective amount of the receptor molecule is also present. That effective amount is typically a catalytic amount; i.e., the receptor is used at a molar ratio to the substrate of about 1:2 to about 1:10,000, with a molar ratio of about 1:10 to about 1:1000 being preferred.

The ratio of receptor molecule to substrate typically depends upon the specific activity of the receptor molecule toward the substrate and the purpose of the user in running the reaction. Thus, where the product is desired, a relatively higher concentration of receptor and higher receptor to substrate ratio are used. Where the reaction mechanism or kinetics of the reaction are being studied, a lower concentration and ratio are typically used. A stoichiometric amount of receptor or more can also be used, but since the receptor is a catalytic molecule, use of even a stoichiometric amount can be wasteful. Thus, at least a catalytic amount of the receptor is utilized.

The cofactor portion of the second immunoligand (the polyvalent metal ion and first coordination ligand) can be present in an amount equal to that of the receptor molecule to an amount aobut ten-fold greater than the substrate. The amount used in a specific reaction can vary with the rate of reaction desired and the dissociation constant of the receptor-cofactor immunocomplex.

It is usually desirable for the cofactor to remain bound in the antibody combining site whereas the substrate can diffuse in, react and the reaction product(s) diffuse out. Using receptor molecules, cofactors and substrates as described herein, the cofactor is typically provided at a concentration of about 0.1 to about 10 times that of the substrate, and more preferably at a ratio to substrate of about 1:1 to about 5:1.

V. Results

The discussion that follows relates to the preparation and use of receptor molecules that exhibit peptidase activity. As noted earlier, those receptor molecules are referred to as absin molecules or absins.

Figure 1:
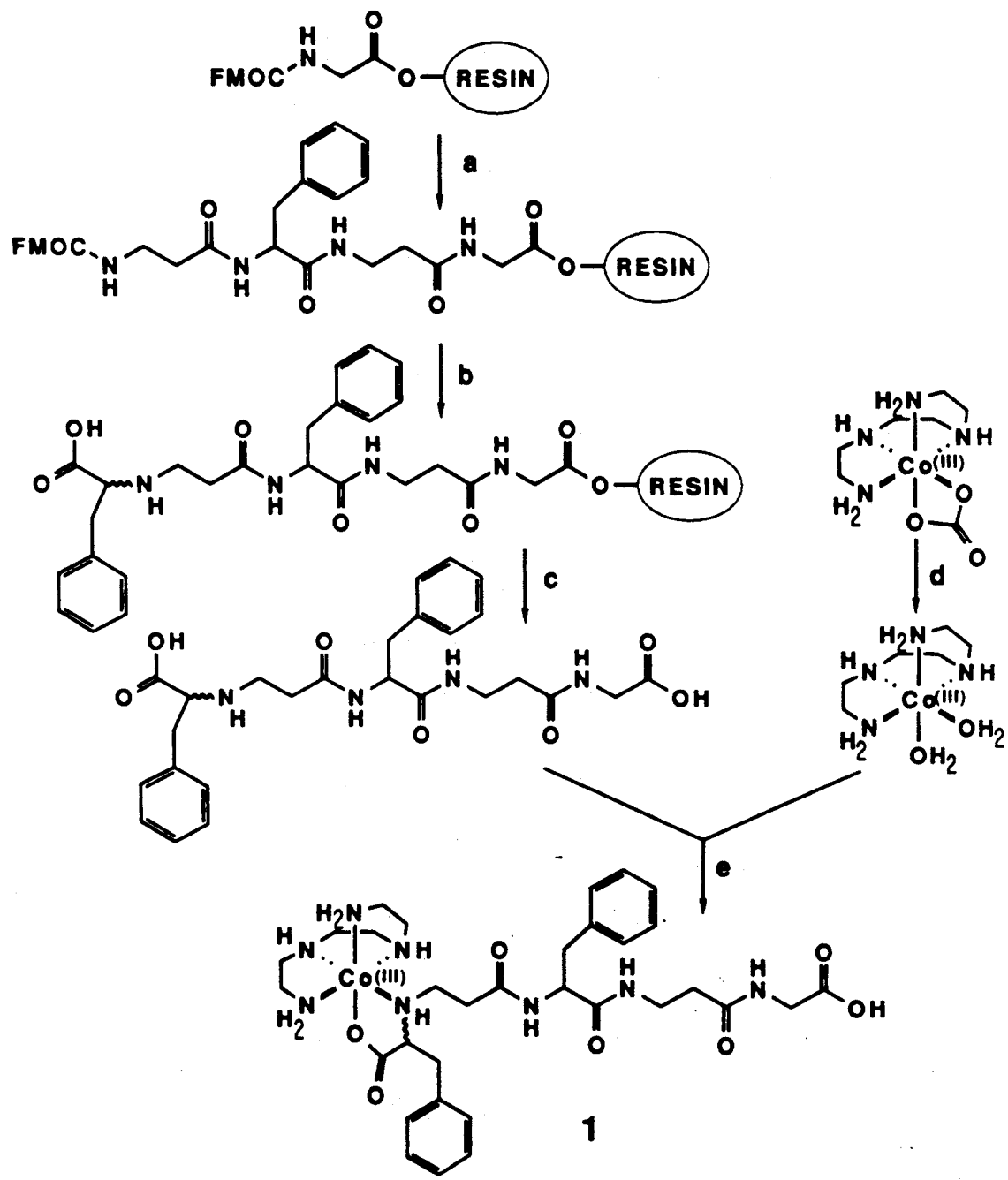
FIG. 1 is a schematic representation that illustrates the synthesis of the haptenic unreactive organic structure 1 that was used as the immunogenic, first immunoligand, and also as an inhibitor. The peptide portion of the molecule was synthesized by solid phase synthesis methods and was built from the carboxy-terminus toward the amino-terminus, using a step-wise addition process.

In order to induce the absins that are utilized illustratively herein, the hapten 1 used for immunization consisted of a relatively kinetically inert Co(III)(trien) moiety complexed to the secondary amino acid site of a four residue peptide 30 (FIG. 1). Since a kinetically inert metal would probably not substitute ligands quickly enough to be an ideal hydrolysis cofactor [Co(III) complexes can cleave amide bonds, but the kinetically inert nature of the complexes results in stoichiometric rather than catlytic cleavage. See, for example, Collman et al., *J. Am. Chem. Soc.* 85:3039 (1963)] it was thought that monoclonal antibodies to 1 would have a somewhat promiscuous combining site capable of accommodating trien complexes of not only Co(III), but also kinetically labile metals such as Zn(II) or Fe(III) which should be hydrolytically active cofactors. Thus, as noted earlier, the Meares et al. U.S. Pat. No. 4,722,892 and Reardon et al., *Nature*, 318:265–268 (1985) disclosures teach that antibodies induced by an In(III) EDTA complex bound several different EDTA-metal complexes.

The antibody combining sites of the absins induced by hapten 1 were intended to bring metal complex and peptide together in an appropriate geometry then allow and facilitate the metal-catalyzed peptide hydrolysis reaction, and finally, to release the products. In this regard, the hapten 1 differs from a true transition state analog in that there is no portion of the hapten molecule which exactly resembles the presumed metal-bound tetrahedral atom of the reaction transition state. The molecule was designed more as a template around which a complementary absin combining site would be produced that was capable of simultaneouly binding an octahedral metal cofactor complex and the substrate peptide together as an immunoligand.

Depending on the conformation of immunogen (peptide-containing hapten 1), it was anticipated that the absin combining site would accommodate the scissile bond of the peptide portion of the antigenic immunoligand in an orientation that would place the carbonyl group close to the metal atom of a simultaneously bound metal trien complex.

The metal complex could then facilitate amide bond hydrolysis by (a) binding the carbonyl oxygen atom, thus polarizing the carbonyl group, (b) promoting the nucleophilic attack of a metal-bound hydroxide species (water or hydroxide ion), or (c) by both operating together. Either pathway, or a combination of the two, would lead to a metal-bound tetrahedral intermediate. Breakdown of this metal-bound tetrahedral intermediate along with protonation of the leaving amine function, and release of the products completes the hydrolysis reacion.

Hapten 1 was covalently attached to keyhole limpet hemocyanin (KLH) and 129G1X* mice were immunized with the resulting conjugate utilizing a standard immunization regimen, discussed hereinafter. One-half of the spleen from the highest responding mouse was harvested and used for fusion with SP2/0 myeloma cells. A total of thirteen hybridomas were identified and maintained that secreted monoclonal antibodies that specifically bound hapten 1 as determined by ELISA, also discussed hereinafter.

Competition ELISA studies indicated that the thirteen antibodies could accommodate a variety of trien metal complexes in their combining sites, and subtle differences in metal binding specificities between different antibodies were observed. In general, Cd(II)(trien), Co(III)(trien), Cu(II)(trien), Fe(III)(trien), Ni(II)(trien), Pd(II)(trien), and Zn(II)(trien) were bound with highest affinity, although binding to metal complexes such as Co(II)(trien), Ga(III)(trien), Sc(III)(trien), In (III)(trien), La(III)(trien), Tb(III)(trien), Yb(III)(trien), Mg(II)(trien), Mn(II)(trien) and Lu(III)(trien) could also be detected with some of the antibodies. Negligble amounts of competition wre observed when only metal salt was added (no trien ligand).

Each of the thirteen monoclonal antibodies was screened for peptide bond cleavage (amide hydrolysis) activity with the six substrate peptides 2–7 (below) using several different trien metal complexes as possible cofactors for the immunoligand formed. A rapid and sensitive peptide cleavage assay was developed that detected the free amine groups revealed during any peptide bond (amide) hydrolysis of the substrates.

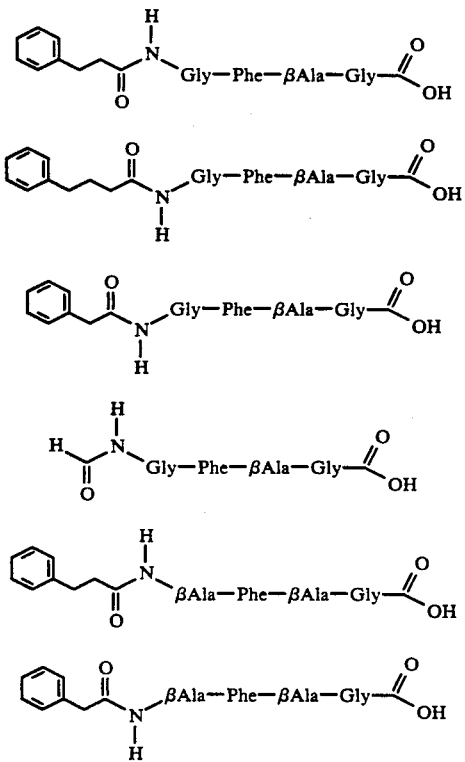

The assay involved spotting the reaction mixture on a silica (thin layer chromatography) (TLC) plate that was then eluted with a 1:4 water:methanol (v:v) solvent mixture. Any hydrolyzed peptide product eluted near the solvent front, whereas absin and metal-trien cofactor remained at the origin. After elution, the plate was sprayed with an acetone solution of fluorescamine, and any fluorescent green material (long wave UV) near the solvent front indicated substrate hydrolysis. As little as 2 micromoles (uM) of product amine could be detected with this procedure. The routine nature of the assay facilitated investigation of a large number of reaction parameters with each absin.

Several of the antibodies exhibited substantial cleavage of peptide substrates 2 and 3 using several of the metal ion complex cofactors. The trien complexes of Zn(II), Fe(III), Ga(III), Cu(II) and Ni(II) were particularly effective cofactors. Peptides 4–7 were not substrates for any of the antibodies. One absin, 28Fll was selected for immediate study and the peptide hydrolysis activity of this absin has been analyzed in detail using peptide 2.

In a typical reaction, 10 uM 28Fll was admixed with 3 mM trien metal ion complex along with 1.2 mM substrate peptide in 75 mM phosphate buffer, and the resulting admixture maintained for a period of days for the reaction to proceed. The reaction strictly required the fully complemented system of absin and antigenic immunoligand [metal(trien) and substrate]. Optimum cleavage was observed in the pH value range 6.0–7.5 with most of the metals, however different metals displayed different pH value optima.

As can be seen in FIG. 2, after five days at 37 degrees C and pH 6.5, cleavage of peptide 2 was observed with the trien metal ion complexes of (in decreasing relative order of activity) Zn(II), Ga(III), In(III), Fe(III), Cu(II), Ni(II), Lu(III), Mn(II) and Mg(II). Small, but reproducible, amounts of cleavage were observed with antigenic immunoligands comprised of the trien metal ion complexes of Al(III), and Co(II) and peptide 2. No cleavage of peptide 2 by receptor 28Fll was observed without a cofactor, when trien alone was used, or with 28Fll plus the trien complexes of Cd(II), Pd(II) Sc(III), Tb(III) and Yb(III). Substrate 3 had a similar metal dependence to the cleavage reaction of substrate 2.

Zn(II)(trien) was observed to be the most efficient metal cofactor complex, exhibiting optimal efficiency at a concentration of 1.5 mM. The catalyzed hydrolysis of substrate 2 with the Zn(II) (trien) cofactor was optimal between pH 6.0 and 8.0, and at NaCl concentrations below 800 mM.

Several lines of evidence confirm that the proteolytic activity (peptide bond cleavage) observed using receptor 28Fll is due to the absin combining site. First, the substrate specificity is in accord with the structure of the hapten 1 used in the immunogenic immunoligand. Second, purified Fab' fragments produced by limited pepsin proteolysis of receptor 28Fll retained full catalytic activity. Third, the trien ligand was shown to be a requirement of the hydrolysis reaction since Zn(II) alone exhibited only minimal activity. [The fact that any cleavage was observed at all without trien probably reflects the limited ability of the absin combining site to accommodate an aquated Zn(II) complex.] Fourth, the reaction was effectively inhibited by hapten 1, and hapten inhibition is a characteristic of catalytic antibodies. All of the data are consistent with a catalytic hydrolysis reaction taking place in the absin antibody combining site involving the Zn(II) (trien) as a non covalently bound cofactor.

The products of larger scale reactions with peptides 2 and 3 were isolated, and they were shown to be the result of specific cleavage between the Gly-Phe bond of each. Using 4 mg of peptide substrate, a reaction using 3 mM of Zn(II) (trien) and 10 uM of receptor 28Fll was permitted to go to completion over a period of 8 days. This corresponds to 400 turnovers per antibody combining site, and therefore a turnover number of $6 \times 10^{-4} s^{-1}$. Only two fragments were observed from the reactions, and were isolated and characterized by NMR (FIG. 3 for peptide 2). The structures of the fragments could only have resulted from a single cleavage between the glycine and phenylalanine of each substrate.

A detailed mechanistic interpretation of this absin catalyzed peptide hydrolysis reaction probably depends upon a conformational analysis of hapten 1 and/or the peptide substrates. Since the metal trien complex was shown to be a required cofactor of an antigenic immunoligand, it is reasonable to assume the scissile bond of the peptide substrate is directly coordinated to the metal at some point during the reaction.

On first inspection, the Gly-Phe bond of peptide substrates 2 and 3 would seem to be somewhat removed from the metal combining site. Preliminary model building has indicated that placing both phenyl rings adjacent to each other in hapten 1 should indeed create an absin combining site that would require binding of peptides 2 and 3 in a geometry that places the scissile amide bond (Gly-Phe) adjacent to the metal binding site.

The peptidase specificity observed is consistent with this model since peptides 4–7 are unlikely to adopt a similar geometry. A conformational analysis of compounds 1-7 is currently under way to help increase understanding of the details of this peptide hydrolysis reaction.

VI. Preparation of Specific Receptors

The receptors useful in the present invention are preferably monoclonal antibodies, although polyclonal antibodies or their combining site portions can be used. A "monoclonal antibody" is a receptor produced by clones of a single cell called a hybridoma that secretes but one kind of receptor molecule. The hybridoma cell is fused from an antibody-producing cell and a myeloma cell or other self-perpetuating cell line.

Techniques for preparing the monclonal antibodies of the present invention are well known. Such receptors were first described by Kohler and Milstein, *Nature*, 256, 495 (1975), which is incorporated herein by reference. Monoclonal antibodies are typically obtained from hybridoma tissue cultures or from ascites fluid obtained from mammals into which the hybridoma tissue was introduced. Both methods are described herein.

Monoclonal receptors are preferred herein because of their unique specificity in binding to a particular epitope such a particular immunizing analog-ligand and reactant ligand, as well as their relatively higehr specific catalytic activity as compared to polyclonal antibodies. Polyclonal antibody preparations can be used herein, but typically have to be separated into fractions that bind to the immunizing analog-ligand and those that bind to extraneous epitopes such as those of the antigenic carrier.

Polyclonal antibodies that bind to the immunogenic immunoligand can be separated by affinity separation using an immunoligand as the affinity sorbant. After admixture and maintenance of an antibody preparation with the affinity sorbant for a time sufficient for appropriate immunoreaction to take place, the affinity sorbant is separated from the remaining portion of the antibody preparation.

The separated, remaining antibody portion bound to the affinity sorbant contains the antibodies that bind to the immunogenic immunoligand, whereas antibodies in the separated remaining portion of the antibody preparation bind to extraneous epitopes. Those affinity-bound antibodies can thereafter be isolated by usual techniques for separating bound entities from affinity sorbants, such as washing the sorbant with glycine-hydrochloride at pH 2.

Idiotype-containing polyamide portions (antibody combining sites) of antibodies are those portions of antibody molecules that include the idiotype, and bind to the ligand or analog-ligand. Such portions include the Fab, Fab' and F(ab')$_2$ fragments prepared from antibodies by well-known enzymatic cleavage techniques. See for example, U.S. Pat. No. 4,342,566 to Theofilopoulos and Dixon, generally, and specifically, Pollack et al. [*Science*, 234, 1570 (1987)]who reported accelerated hydrolytic rates for Fab fragments were the same as those of the native Ig. Inasmuch as the antibodies from which idiotype-containing polyamides are obtained are described as raised against or induced by immunogens, idiotype-containing polyamide (antibody combining site containing) receptors are discussed as being "raised" or "induced" with the understanding that a cleavage step is typically required to obtain an idiotype-containing polyamide from an antibody. Intact antibodies are preferred.

To prepare the receptor molecules used illustratively herein, 6-8 week old 129GIX* mice were immunized with an immunogen prepared by coupling 2.5 mg of the unreactive peptide 1-containing immunoligand in 250 ul of DMF to 2 mg of KLH in 750 ul of 0.01 m sodium phosphate buffer, pH 7.2, while stirring at 4 degrees C. for 1 hour to form a conjugate using 1-ethyl-3-(3-dimethylaminopropyl)carbodiimide following the instructions in the Pierce Chemical Company Catalogue. An inoculum prepared containing 600 ul of a conjugate solution, 900 ul of PBS buffer and 1500 ul of complete Freund's adjuvant (3000 ul) was administered at 500 ul per mouse to provide 100 ug of conjugate per mouse. Administration was by i.p. injection.

The mice were given booster injections i.p. two weeks after the initial immunizations. The booster inoculum was prepared to contain 300 ul of the conjustate solution, 1200 ul of PBS buffer and 1500 ul of an alum adjuvant dispersion (3000 ul). Each mouse received 500 ul to provide 50 ug of conjugate per mouse.

Four weeks thereafter, the mice were boosted again. Here, the inoculum contained 100 ul of the conjugate solution and 300 ul of PBS buffer. Each mouse received 200 ul i.p. that contained 100 ug of the conjugate.

An ELISA was used to screen the polyclonal antibodies produced by the immunized mice. The antigen used was a conjugate prepared by linking the haptenic peptide 1 to bovine serum albumin (BSA) following the same procedures described for preparation of the KLH conjugate. The polyclonal antibodies were also screened using the first immunoligand as an inhibitor to assure that specific binding was being observed. Positive binding was assayed using peroxidase-labeled goat anti-mouse IgG+IgM. Binding assays were also carried out in the presence of free haptenic peptide 1 as an inhibitor to help assure that the observed binding was specific.

Cells from one-half of the spleen of the mouse whose antibodies exhibited the highest titer in the ELISA were fused with myeloma P3X63AG8.653 (ATCC CRL 1580) cells in 10 percent fetal calf serum. Cells from the other one-half of the spleen were fused with SP2/0-Ag14 (ATCC CRL 1581) myeloma cells in 1 percent nutridoma and 2 percent BSA. Standard fusion techniques were used.

Cells from each of the fusions were plated into ten 96-well plates. About 10 percent of the wells from the P3X63 fusion showed growth in HAT-DMEM medium with no well supernatants exhibiting positive binding in the above ELISA. About 30 percent of the wells from the SP2/0 fusion exhibited growth in HAT-DMEM medium. Of the 300 wells with growth, 35 well supernatants were positive in the ELISA. Of those 35 initial positives, 15 kept their activity through subcloning and were introduced into mice for the production of ascites.

Those fifteen hybridomas have been analyzed for their light and heavy chain make-ups. Twelve were found to be kappa, gamma 1; two lambda, gamma 1; and one kappa, mu. Thirteen of the fifteen were assayed for possible catalytic activity, and were found to exhibit such activity, with two hybridomas still growing in the mice. It is now known that the thirteen hybridomas contain at least two different hybridomas, and work is being carried out to determine if the remaining eleven hybridomas are the same or different from those two identified cell lines.

Each of the thirteen hybridomas was injected into pristane-primed BALB/c X 129GIX* mice to generate ascitic fluid. The monoclonal antibodies were purified from the ascites by precipitation with saturated ammonium sulfate, followed by ion exchange chromatography on DEAE-Sephadex, and then affinity chromatography on Prot-G Sepharose. Protein concentrations were determined by the Lowry method [*J. Biol. Chem.*, 193:265 (1951)].

The resulting receptor-containing aqueous solutions were concentrated by Amicon ultrifiltration and dialyzed into 5 mM phosphate buffer containing 20 mM NaCl, and 20 mM EDTA at pH 7 to remove metal ions. The EDTA-containing solutions were then dialyzed into a buffer of 5 mM phosphate and 20 mM NaCl at pH 7 for use. Stock solutions of receptor 28F11 were prepared by concentration of the above-prepared solutions in the Amicon filter to a concentration of about 4 to about 20 mg/ml.

The Fab' fragment portion was prepared as follows. The purified monoclonal receptor 28F11 (28 mg) was dissolved in 0.1M citrate buffer at pH 3.7 to provide a protein concentration of 1 mg/ml. Small amounts of 1.0M citrate buffer were added to the receptor solution to adjust the pH value to 3.7.

Thereafter, 1.4 mg of pepsin were added to the pH-adjusted receptor solution and the resulting admixture maintained at 37 degrees C. for a period of 2 hours and 20 minutes to form F(ab')$_2$ fragments. The reaction was stopped by adding 2 ml of 3M Tris-HCl buffer having a pH value of 8.0 that raised the pH value of the solution to 7.5.

Cysteine (36.4 mg) was added to the above F(ab')$_2$-containing solution, and the resulting admixture was maintained at 22 degrees C. for a time period of 3 hours. Sufficient iodoacetamide was then added to provide a final concentration of 30 mM iodoacetamide. The iodoacetamide-containing solution was maintained at 4 degrees C. for 4 hours in the absence of light. The reaction mixture was then dialyzed into a buffer containing 200 mg of sodium acetate in a 10 mM phosphate buffer at pH 6.8, while maintaining the receptor protein concentration at 1 mg/ml.

The resulting Fab' antibody fragment portions were purified by size exclusion chromatography on silica HPLC using a TSKG-300 column and the last-named buffer. Eluting fractions were assayed by SDS-PAGE for the appropriately-sized, desired Fab' fragments.

The Fab' fragment-containing fractions were dialyzed into a buffer containing 20 mM NaCl, 5 mM EDTA and 5 mM phosphate at pH 7, to remove multivalent metal ions. The EDTA was thereafter removed by dialysis into a buffer containing 20 mM NaCl and 5 mM phosphate, at pH 7. Stock solutions of the Fab' antibody portions were concentrated in an Amicon ultrafiltration apparatus to a protein concentration of about 4 to about 10 mg/ml.

One of those hybridomas, as an example of the class, was deposited at the American Type Culture Collection (ATCC), 12301 Parklawn Drive, Rockville, Md. That hybridoma, designated 28F11, and having ATCC accession number HB9971, was deposited on Jan. 13, 1989.

The above deposit was made in compliance with the Budapest Treaty requirements that the duration of the deposits should be for 30 years from the date of deposit or for 5 years after the last request for the deposit at the depository or for the enforceable life of a U.S. patent that matures from this application, whichever is longer.

The hybridomas will be replenished should they become non-viable at the depository.

For another preparation of the receptor molecules, the gene that encodes an antibody combining site-forming fragment can be obtained from any cell that produces an antibody molecule that immunoreacts as discussed herein. A preferred cell is a hybridoma cell.

For examples of general recombinant DNA cloning methods, see *Molecular Cloning*, Maniatis et al., Cold Spring Harbor Lab., N.Y., 1982; *DNA Cloning*, Glover, ed., IRL Press, McLean Va. (1985). For the genomic cloning and expression of immunoglobulin genes in lymphoid cells, see Neuberger et al., *Nature*, 312:604–8 (1984); Ochi et al., *Proc. Natl. Acad. Sci. USA*, 80:6351–55 (1987); and Oi et al., *Proc. Natl. Acad. Sci. USA*, 80:825–29 (1983). For cloning of immunoglobulin genes from hybridoma cells and expression in Xenopus oocytes, see Roberts et al., *Protein Engineering*, 1:59–65 (1986), and see Wood et al. for expression in yeast. *Nature*, 314:446–9 (1985).

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A monoclonal absin molecule composition comprising receptor molecules containing an antibody combining site that immunologically binds to a first peptide-containing immunoligand forming an immunocomplex with a dissociation constant of $10^{-8}$ or less, and to a second peptide-containing immunoligand and exhibits catalytic hydrolase activity toward a predetermined peptide bond of said second immunoligand, said first immunoligand comprising a kinetically inert metal ion coordination complex that has a structure that is represented by the formula

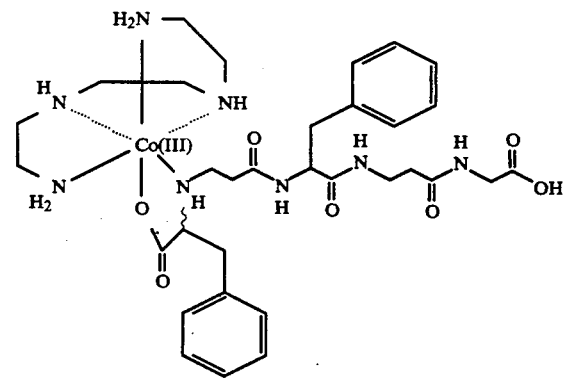

said second immunoligand comprising a kinetically labile metal ion coordination complex that contains a second metal ion different from Co(III) of said first coordination complex that is coordinated to two or more individual metal ion coordination ligands, the first of said coordination ligands being triethylenetetramine and the second of said individual coordination ligands having a structure that is represented by the formula

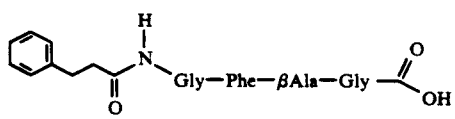

or

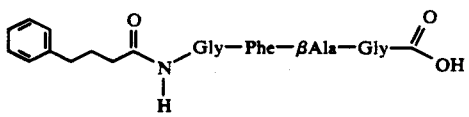

wherein the metal ion of said kinetically labile, second immunoligand is a member of the group consisting of Zn(II), Fe(III), Co(II), Cu(II), Ga(III), Lu(III), Lu(III), In(III), Al(III), Mn(II), NI(II) and Mg(II).

2. A method of hydrolyzing a preselected peptide bond comprising the steps of:

a) admixing in an aqueous medium a catalytically effective amount of an absin molecule that contains an antibody combining site that immunologically binds to a first peptide-containing immunoligand with a dissociation constant of $10^{-8}$ or less and to a second peptide-containing immunoligand, and exhibits catalytic hydrolase activity toward a predetermined peptide bond of said second immunoligand, said first immunoligand comprising a kinetically inert metal ion coordination complex that is represented by the formula said second immunoligand comprising a kinetically labile metal ion coordination complex that contains a second metal ion different from Co(III) that is coordinated to two or more individual metal ion coordination ligands, the first of said coordination ligands being triethylenetetramine, and the second of said individual coordination ligands having a structure that is represented by the formula or said second metal ion and the first individual coordination ligand thereof comprising a cofactor, the reactive peptide of said second individual coordination ligand thereof constituting a substrate, and wherein the metal ion of said kinetically labile, second immunoligand is a member of the group consisting of Zn(II), Fe(III), Co(II), Cu(II), Ga(III), Lu(III), In(III), Al(III), Mn(II), Ni(II), and Mg(II).

3. Hybridoma 28Fll having the ATCC accession number HB 9971.

4. The catalytic monoclonal antibody combining site-containing molecule that is secreted by the hybridoma having the ATCC accession number HB 9971.

* * * * *